(12) United States Patent
Tanaka et al.

(10) Patent No.: US 8,593,625 B2
(45) Date of Patent: Nov. 26, 2013

(54) EXAMINING APPARATUS AND EXAMINING METHOD

(75) Inventors: Kazumasa Tanaka, Hitachinaka (JP); Hiroyuki Yamashita, Fujioka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 55 days.

(21) Appl. No.: 13/202,717

(22) PCT Filed: Nov. 19, 2009

(86) PCT No.: PCT/JP2009/006211
§ 371 (c)(1),
(2), (4) Date: Aug. 22, 2011

(87) PCT Pub. No.: WO2010/113228
PCT Pub. Date: Oct. 7, 2010

(65) Prior Publication Data
US 2011/0304848 A1 Dec. 15, 2011

(30) Foreign Application Priority Data
Mar. 31, 2009 (JP) ................................. 2009-083999

(51) Int. Cl.
*G01N 21/00* (2006.01)
(52) U.S. Cl.
CPC ..................................... *G01N 21/00* (2013.01)
USPC ................... 356/237.2; 356/237.1; 356/237.5
(58) Field of Classification Search
CPC ..................................................... G01N 21/00
USPC ........................................... 356/237.1–237.5
See application file for complete search history.

(56) References Cited

U.S. PATENT DOCUMENTS 8,098,372 B2 * 1/2012 Eitan et al. ................. 356/237.2
8,358,406 B2 * 1/2013 Ikota et al. ................. 356/237.1
(Continued)

FOREIGN PATENT DOCUMENTS

JP 11-311608 11/1999
JP 11-311608 A 11/1999
(Continued)

OTHER PUBLICATIONS

Japanese Office Action issued in Japanese Patent Application No. JP 2010-055789 dated Apr. 2, 2013 with English Translation.

*Primary Examiner* — Michael P Stafira
(74) *Attorney, Agent, or Firm* — McDermott Will & Emery LLP

(57) ABSTRACT

When examination at a scan speed equal to or higher than the line rate of the sensor such as a TDI sensor is carried out, the line rate of the TDI sensor is asynchronous with the scan speed, and the image is blurred. Therefore, a TDI sensor cannot be used at a scan speed equal to or higher than the line rate of the TDI sensor. This problem has not been considered. To solve the problem, high-speed examination irrespective of the line rate of the TDI sensor is enabled. To control the line rate of the TDI sensor and stage scan speed asynchronously and to solve the problem of the image addition variation due to the charge accumulation of the TDI sensor, the object to be examined is irradiated with thin-line illumination, and only a given pixel line of the TDI sensor is made to receive light scattered by the object to be examined. The aspect ratio of the detection pixel size can be controlled by the speed ratio between the line rate of the TDI sensor and the stage scan speed.

21 Claims, 5 Drawing Sheets

(56) References Cited

U.S. PATENT DOCUMENTS

| | | |
|---|---|---|
| 2002/0030807 A1 | 3/2002 | Maeda et al. |
| 2004/0252296 A1 | 12/2004 | Tojo et al. |

FOREIGN PATENT DOCUMENTS

| | | |
|---|---|---|
| JP | 2000-099702 | 4/2000 |
| JP | 2000-105203 | 4/2000 |
| JP | 2001-208694 | 8/2001 |
| JP | 2002-039960 | 2/2002 |
| JP | 2004-301751 | 10/2004 |
| JP | 2005-241290 | 9/2005 |
| JP | 2005-300553 | 10/2005 |
| JP | 2006-084189 | 3/2006 |
| JP | 2008-145226 | 6/2008 |

* cited by examiner

SYNCHRONOUS ACCUMULATION TO TRANSFER RATE OF TDI: HIGH SENSITIVITY

STAGE SPEED > ASYNCHRONOUS TO TRANSFER RATE OF TDI

EXAMINING APPARATUS AND EXAMINING METHOD

RELATED APPLICATIONS

This application is the U.S. National Phase under 35 U.S.C. §371 of International Application No. PCT/JP2009/006211, filed on Nov. 19, 2009, which in turn claims the benefit of Japanese Application No. 2009-083999, filed on Mar. 31, 2009, the disclosures of which Applications are incorporated by reference herein.

TECHNICAL FIELD

The present invention relates to an examining apparatus and an examining method or, for example, to an examining apparatus and an examining method for detecting foreign objects, scratches, defects, contaminations, etc. which exist on the surface of an object to be examined such as a semiconductor wafer.

BACKGROUND ART

With regard to conventional examining apparatuses and examining methods for detecting defects present on the surfaces of objects to be examined such as semiconductor wafers it has been disclosed in JP-A-2001-208694 (Patent Literature 1) that an exposure time of a photoelectric device is varied in addition to varying the number of added lines in processing of a sample image by TDI based on a light image magnification such that the number of added lines is decreased when an incident light amount is large in a low magnification and the number of added lines is increased when the incident light amount is small in a high magnification. Further, JP-A-2002-39960 (Patent Literature 2) has disclosed that a charge accumulation time can be changed and the number of stages can also be switched over as a multi-tap configuration by using a TDI sensor of variable stages. Furthermore, JP-A-2004-301751 (Patent Literature 3) has disclosed that the number of accumulation stages for a transmitted light sensor and the number of accumulation stages for a reflected light sensor are made different (or can be specified) by using the TDI sensor as a transmitted light sensor and a function to be able to adjust a luminance, an expansion and contraction (magnification), a distortion, and a rotation can be provided to either image. In the similar examining apparatus, JP-A-2006-84189 (Patent Literature 4) has disclosed that a scan speed is made high in using a high magnification lens and is made low in using a low magnification lens when moving an imaging unit to scan the object to be examined and that a camera unit has a TDI sensor and a lens switching device to control a moving speed in response to switching over the high and low magnification lenses. Moreover, JP-A-2000-105203 (Patent Literature 5) has disclosed that a TDI sensor is used as an image sensor and a determination criterion can be set in an image processing unit depending on an area priority mode, a standard mode, and a sensitivity priority mode.

CITATION LIST

Patent Literature

PATENT LITERATURE 1: JP-A-2001-208694
PATENT LITERATURE 2: JP-A-2002-39960
PATENT LITERATURE 3: JP-A-2004-301751
PATENT LITERATURE 4: JP-A-2006-84189
PATENT LITERATURE 5: JP-A-2000-105203

SUMMARY OF INVENTION

Technical Problem

However, in the techniques disclosed in the above-mentioned Patent Literature 1 to 5, when examining with the scan speed equal to or faster than the line rate of the sensor (for example, the TDI sensor), a line rate becomes asynchronous with the scan speed of a sensor (for example, a TDI sensor) and the image is blurred; therefore, there has not been consideration for a problem such that they cannot be used at the scan speed equal to or faster than the line rate of the sensor (for example, the TDI sensor).

In order to solve the above-mentioned problem, the present invention has an objective to enable a high speed examination without being influenced by the line rate of the sensor (for example, the TDI sensor).

Solution to Problem

One aspect of the present invention is that a thin-line illumination is irradiated on an object to be examined and a predetermined pixel area (for example, a predetermined pixel line alone) of a sensor (for example, a TDI sensor) receives scattered light from the object to be examined in order to control the line rate of the sensor (for example, the TDI sensor) and a stage scan speed asynchronous and to solve the problem of shift in image addition due to the charge accumulation of the sensor (for example, the TDI sensor).

Another aspect of the present invention is that an aspect ratio of a detection pixel size can be controlled by a speed ratio of the line rate of the sensor (for example, the TDI sensor) and the stage scan speed.

Advantageous Effects of Invention

According to one aspect of the present invention, a scan speed faster than the line rate of a sensor (for example, a TDI sensor) becomes possible so that a high speed examination equal to or faster than the line rate of the sensor (for example, the TDI sensor) can be achieved.

DESCRIPTION OF EMBODIMENTS

Hereinafter, embodiments of the present invention will be described with reference to the drawings.

Figure 1:
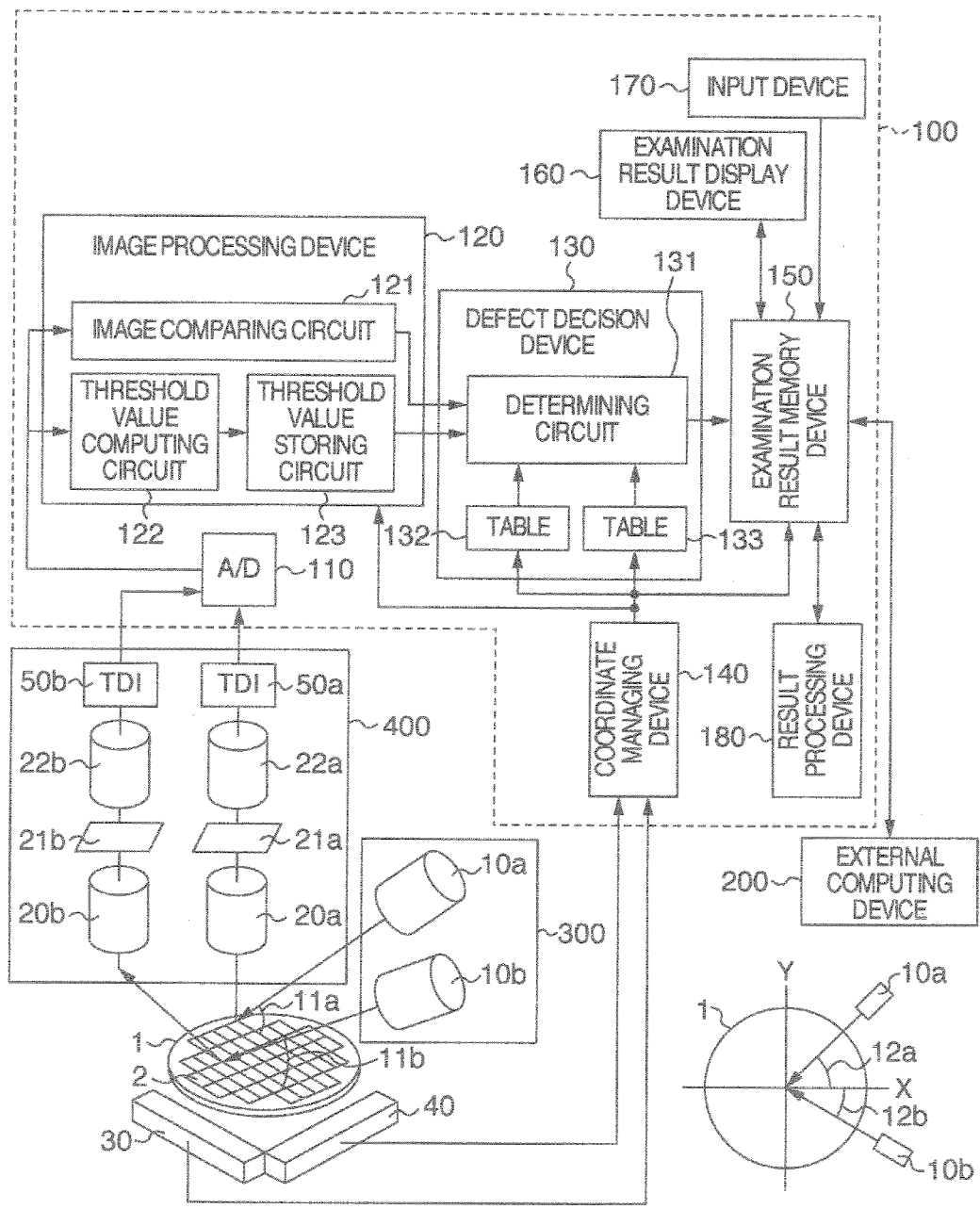
FIG. 1 is a schematic diagram of an examining apparatus associated with one embodiment of the present invention.

FIG. 1 is a schematic diagram of an examining apparatus associated with one embodiment of the present invention. The examining apparatus shown in FIG. 1 is provided with an illumination unit 300, a detection unit 400, an X scale 30, a Y scale 40, and a processing device 100. It may also be provided with an external computing device 200. In the present embodiment, an example is described where an optical examining apparatus using a dark-field image is applied to the examining apparatus of the present invention.

An examining method implemented by the present examining apparatus will be described.

Figure 2:
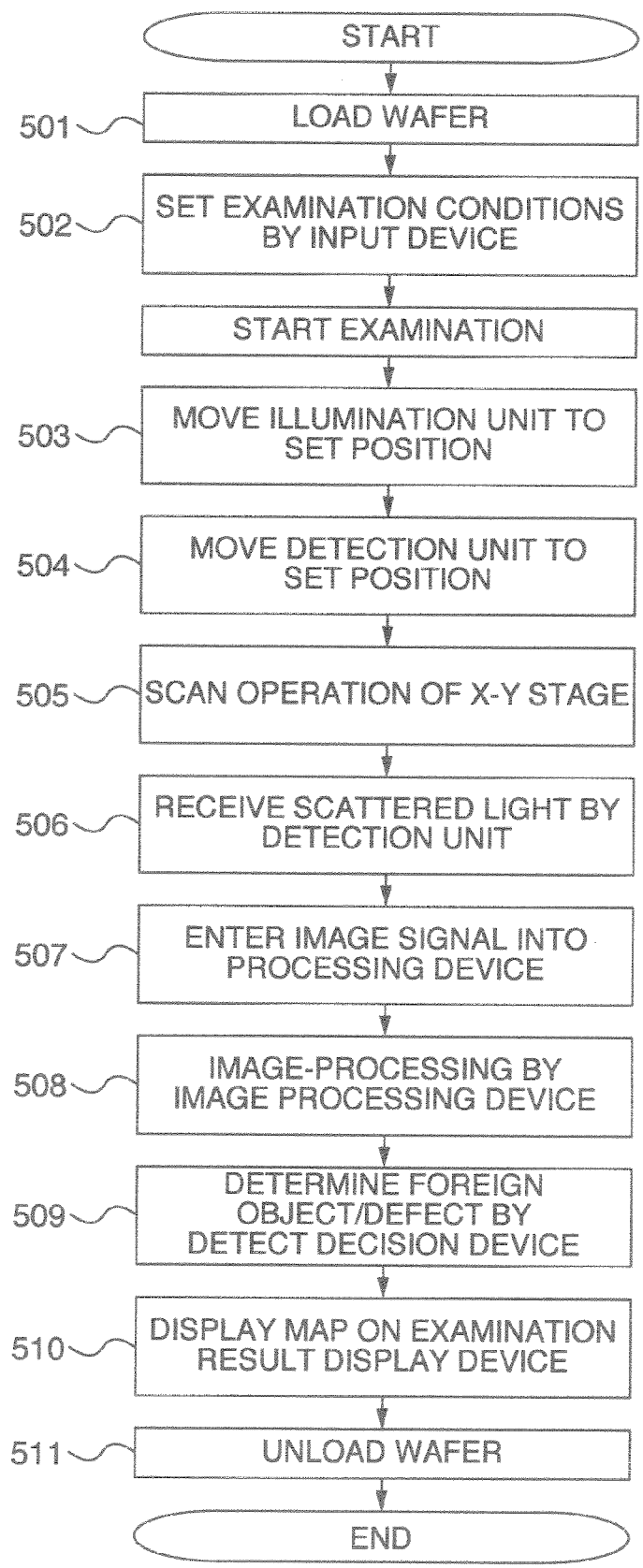
FIG. 2 is a flow diagram of an examining method for the examining apparatus associated with one embodiment of the present invention.

FIG. 2 is a flow diagram of an examining method for the examining apparatus associated with one embodiment of the present invention. First, at a step 501, a wafer is loaded on an X-Y stage in the examining apparatus. Next, at a step 502, examination condition data such as operation speeds of the illumination unit 300, the detection unit 400, and the X-Y stage is set from an input device 170 to start examination of the wafer.

At a step 503 immediately after starting the examination, the illumination unit 300 moves to an examination condition set position. Further, at a step 504 immediately after that, the detection unit 400 moves to the examination condition set position. Once the steps 503 and 504 are complete, an examination light is irradiated on the surface of the wafer 1 from an illumination measure 10a and the X-Y stage starts a scan operation at a step 505 to scan the entire surface of the wafer 1.

At a step 506, the examination light irradiated on the surface of the wafer 1 is scattered by patterns and defects present on the surface of the wafer 1 and the scattered light is received by the detection unit 400; the intensity of the scattered light is converted into an electric signal by a detector 50a (using a TDI sensor in the embodiment of the present invention) and output as an image signal to the processing device 100 at a step 507.

After image-processing by an image processing device 120 in the processing device 100 at the step 508, scattered lights determined as a group of defect candidates from data which is image-processed in a defect decision device 130 at a step 509 are output as examination results to an examination result memory device 150. At a step 510, the examination results decided as the group of defect candidates are displayed on an examination result display device 160 at a step 510. At a step 511, the wafer is unloaded and the examination ends.

A TDI (Time Delay Integration) sensor is used as a sensor in the detection unit. The TDI sensor is configured by N pixels×M lines and charges are shifted and added in a line direction to accumulate the charges of M times. Using this feature images of high sensitivities with low noises can be acquired by making the charge shift speed and a moving speed of an object to be examined the same. Incidentally, the maximum charge shift speed in the line direction of the TDI sensor is referred to as a line rate.

In an examining apparatus of this type, usually when a pattern which constitutes a chip is formed on the surface of the wafer, an image signal is generated from the intensity of the detected scattered light, an image signal of an examination area (an examined chip or an examined shot) is compared with an image signal of a reference area (a reference chip or a reference shot), a spot at which a difference between them is equal to or greater than a threshold value is determined as a foreign object. As the reference area, either an adjacent area (an adjacent chip or an adjacent shot) of the examination area or a good product area prepared in advance (a good product chip or a good product shot) is used.

Besides, a required sensitivity and a required examination time for the examining apparatus vary widely depending on the types of wafers, processing steps, and managing methods by users.

Figure 4:
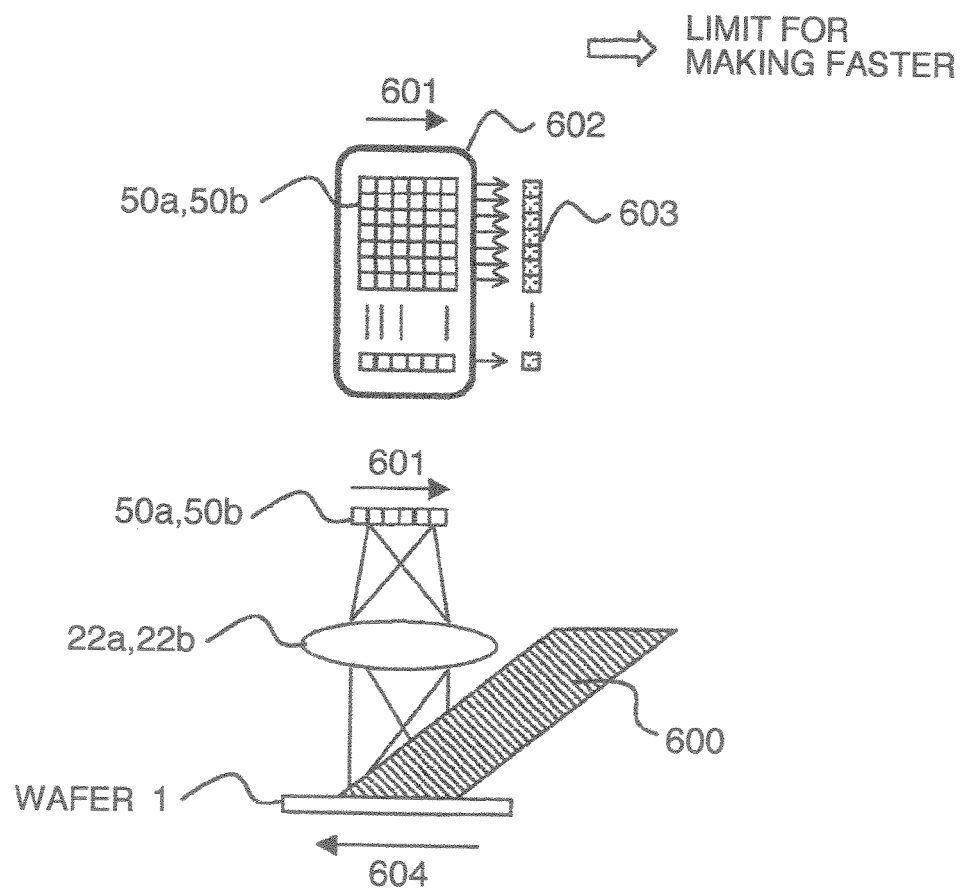
FIG. 4 is a diagram for explaining a TDI sensor synchronous scan examining method.

First, a general TDI sensor synchronous scan examining method will be described below. FIG. 4 is an explanatory diagram of the TDI sensor synchronous scan examining method. An illumination light 600 is a wide-width illumination beam. In a light-receiving area 602 of the TDI sensor on which the scattered light from the wafer surface is incident, it is possible to accumulate the charges of the scattered light at every repetitive transfer since a stage scan speed 604 is coincident (synchronous) with a charge transfer speed in a transfer direction 601 of the TDI sensor 50a.

For this reason, it is possible to acquire a large output image signal 603 in relation to a fine-sized object compared with a conventional CCD of the line sensor type by an effect of accumulating the electric charge. In consequence, it is possible to make a minimum detectable size small.

The examining method according to a TDI sensor asynchronous scan will be described below as one of aspects of the present invention.

Figure 5:
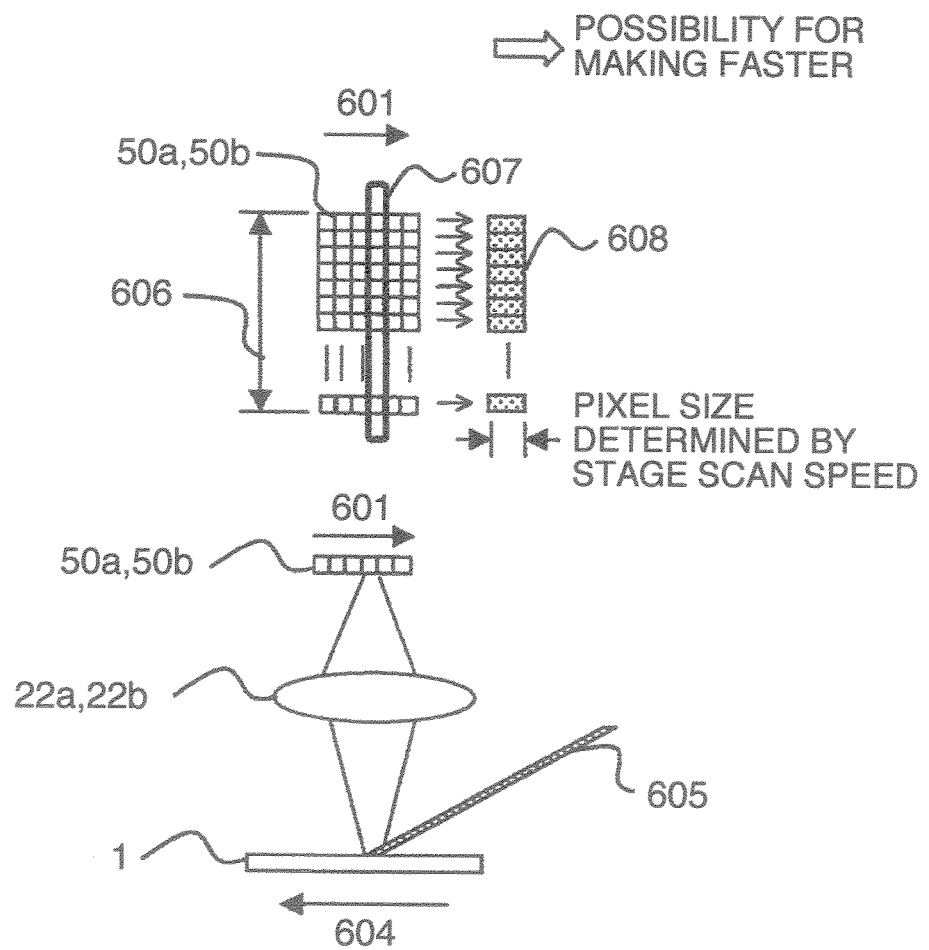
FIG. 5 is a diagram for explaining a TDI sensor asynchronous scan examining method.

FIG. 5 is an explanatory diagram of a TDI sensor asynchronous scan examining method. There is a method of making the stage scan speed 604 faster than the charge transfer speed in the transfer direction 601 of the TDI sensor 50a so that the examination speed is made fast. This method is referred here as the TDI sensor asynchronous scan examination. In this method it measures over a distance (pixel size) longer than a measurement range of the electric charge transfer speed in the transfer direction 601 of the TDI sensor 50a because the stage scan speed is made fast; therefore, a measurement pixel size (on the measurement surface) becomes a rectangle as shown by a reference numeral 608. The size of the rectangle varies depending on the stage scan speed. That is, there is an effect of enabling control of an aspect ratio of a detection pixel size with a speed ratio of the line rate of the TDI sensor and the stage scan speed. Also in the examining method, an illumination beam 605 having a thin width (this thin width illumination beam is referred to as thin-line illumination), with which the width of scattered light from the wafer surface becomes either a width of a targeted measurement pixel line 606 or a thinner width than that, is irradiated on the wafer surface in such a way that a light-receiving area 607 of the TDI sensor would not detect information of examination surface other than the targeted measurement pixel line 606.

By using the thin-line illumination for the illumination light in the asynchronous scan examination in which the stage scan speed is made fast, a signal for which the charges of scattered light are not accumulated can be acquired as a detection result, likewise to the conventional CCD of the line sensor type. Therefore, it is possible to acquire the detection result 608 in a high speed scan examination since a charge accumulation time is unnecessary.

Referring back to FIG. 1, the illumination unit 300 is, for example, a laser device for generating an examination light such as laser light having a predetermined wavelength to irradiate the examination light on the surface of the wafer 1, which is an object to be examined. The wafer 1 on the surface of which chips 2 are formed is at least loaded on the X-Y stage so that translation in X-Y directions is possible. By moving the stage to the X and Y directions the examination light irradiated from the illumination unit 300 scans the surface of the wafer 1.

The illumination measure 10a irradiates obliquely with an angle like an elevation angle 11a with respect to the surface of the wafer 1 and is provided with a mechanism to be able to switch over the angle of elevation arbitrarily.

The illumination measure 10a irradiates with an angle like an illumination angle 12a with respect to the surface of the wafer 1 relative to the X-Y directions of the stage and is provided with a mechanism to be able to switch over the angle of the X-Y directions arbitrarily.

The illumination measure 10a is provided with mechanisms used for both switching over the angle of elevation angle described in (1) and switching over the angle of X-Y directions described in (2).

The illumination measure 10a is provided with a mechanism with which a polarization of the illumination light can be switched over arbitrarily depending on the types of the objects to be examined and the sizes of the defects to be detected.

The illumination measure 10a is provided with an automatic adjustment mechanism with which the examination light can always be irradiated on a predetermined spot of the surface of the wafer 1 which is an object to be examined.

Figure 3:
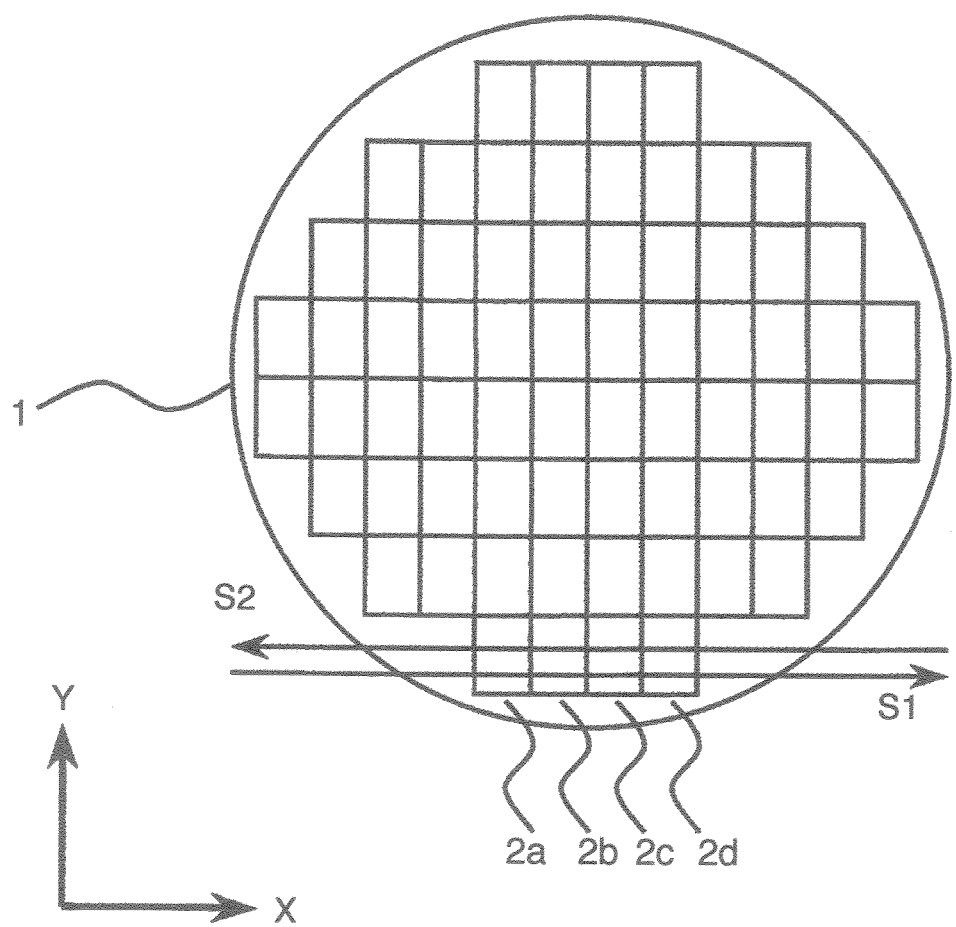
FIG. 3 is a diagram for explaining a scan of an examining light of the examining apparatus associated with one embodiment of the present invention.

FIG. 3 is a diagram for explaining the scan of the examination light in the examining apparatus. When the wafer stage on which the wafer 1 is mounted moves in the X direction, the examination light irradiated from the illumination measure 10a or 10b moves in a direction indicated by an arrow S1 on the surface of chips 2a, 2b, 2c, and 2d formed on the wafer 1 to implement a scan of a single line. Next, the wafer stage moves in the Y direction. Then, when the wafer stage moves in the X direction opposite to that at the time of the scan for the first line, the examination light moves in a direction indicated by an arrow S2 on the surface of the chips 2d, 2c, 2b and 2a to implement a scan for a second line. By repeating these operations the scan on the entire surface of wafer 1 is implemented.

The wafer stage is provided with a mechanism with which a moving speed in the X-Y directions of the stage can be set arbitrarily depending on the types of the objects to be examined and the sizes of the defects to be detected.

Referring back to FIG. 1, the examination light irradiated on the surface of the wafer 1 is scattered by the patterns and defects present on the surface of the wafer 1 to generate the scattered light from the surface of the wafer 1. The detection unit 400 is configured by, for example, a condenser lens, a TDI sensor, and the like to receive the scattered light generated from the surface of the wafer 1, and the detector 50a (using a TDI sensor in the embodiment of the present invention) converts the intensity of the scattered light into an electric signal to output as an image signal to the processing device 100. Incidentally, a CCD sensor may be used as the detector 50a.

An objective lens 20a is a lens to receive and focus the scattered light generated at the surface of the wafer 1 and is provided with a mechanism having a lens individually for the detector 50a.

After the objective lens 20a receives the scattered light generated at the surface of the wafer 1, a spatial filter 21a is provided for cutting off a diffracted light from repetitive patterns on the wafer different from the scattered light from targeted foreign objects, defects, and the like.

The spatial filter 21a is provided with a mechanism in such that a width and a position for cutting off the diffracted light can be switched over arbitrarily depending on intervals of the diffracted light in a shape of an X-Y lattice from repetitive patterns on the wafer different from than the scattered light from targeted foreign objects, defects, and the like.

The spatial filter 21a is also formed in a shape of an X-Y lattice so that the diffracted light in a shape of the X-Y lattice from the repetitive patterns on the wafer can be cut off and provided with the mechanism described in (3).

An imaging lens 22a is provided with a mechanism which can switch over arbitrarily several imaging lenses which have individual magnifications so that a detection sensitivity can be changed depending on the types of the objects to be examined and the sizes of the defects to be detected.

The imaging lens 22a and an image lens 22b may be provided with an imaging lens such as a zoom lens, which is capable of switching over the magnification as a single unit, so that a detection sensitivity can be changed depending on the types of the objects to be examined and the sizes of the defects to be detected.

The illumination unit 300 and the detection unit 400 may be configured by combining plural illumination measures and detection measures having the objective lens 20a, the spatial filter 21a, the imaging lens 22a, and the detector 50a exclusively used for the illumination measure 10a and an objective lens 20b, a spatial filter 21b, the imaging lens 22b, and a detector 50b exclusively used for the illumination measure 10b.

The X scale 30 and the Y scale 40 comprise, for example, laser scales or the like to detect an X direction position and a Y direction position of the wafer stage on which the wafer 1 is mounted, respectively, and output such position information to the processing device 100.

The processing device 100 is provided with an A/D converter 110, the image processing device 120, the defect decision device 130, a coordinate managing device 140, the examination result memory device 150, the examination result display device 160, the input device 170, and a result processing device 180.

The A/D converter 110 converts an image signal of analog signal input from the detection unit 400 incorporating the detector 50a or 50b into an image signal of digital signal and output.

The image processing device 120 is provided with an image comparing circuit 121, a threshold value computing circuit 122, and a threshold value storing circuit 123.

The image comparing circuit 121 is provided with, for example, a delay circuit and a difference detection circuit and serves as a comparing measure for comparing the image signal of the examination area detected by the detection unit 400 with the image signal of corresponding pixel of the reference area to detect a difference between the two. The delay circuit outputs the image signal of the last examination area, on which the irradiation of examination light has already ended, right before an examination area on which the examination light is currently being irradiated in the scan shown in FIG. 2 by receiving the image signal from the A/D converter 110 and delaying it. The difference detection circuit receives the image signal of the examination area on which the examination light is currently being irradiated from the A/D converter 110 and the image signal from the delay circuit to detect and output a difference between the two. In this way, the image comparing circuit 121 compares the image signals of the examination area and the adjacent reference area. When a defect exists on the surface of the examination area, the scattered light scattered by the defect emerges as a difference of the image signals of the mutual adjacent chips.

Incidentally, the image comparing circuit 121 may be provided with a memory storing an image signal data of a good chip prepared in advance instead of the delay circuit and a comparison with the image signal of the examination area of the good product may be conducted.

The threshold value computing circuit 122 functions, for example, based on statistical values of image signals of the pixels corresponding to each examination area, as a threshold computing measure to compute threshold values for comparing with differences of the image signals of the corresponding pixels. In other words, it matches the image signal of the examination area from the A/D converter 110 with the image signal of the respective reference area from the delay circuit for every pixel, calculates an amount of variability (standard deviation) between the respective examination areas, and computes threshold value data used for determining existence of a defect on the basis of the amount of variability.

In the threshold value storing circuit 123 the threshold values entered from the threshold value computing circuit 122 are stored, which are also related to coordinate information of the examination areas entered from the coordinate managing device 140.

The defect decision device 130 is provided with a determining circuit 131 and coefficient tables 132, 133.

In the coefficient tables 132, 133 coefficients for changing the threshold values computed by the threshold value computing circuit 122 are stored, which are also related to the coordinate information on the wafer. The coefficient tables 132, 133 receive the coordinate information from the coordinate managing device 140 and output coefficients corresponding to the coordinate information to the determining circuit 131. The coefficients stored in the coefficient tables 132, 133 are multiplied the threshold value of a corresponding coordinate by when it is output to the determining circuit 131. In this way, the threshold values are flexibly adjusted based on accumulation of past examination/analysis data for places in the examination area or on the wafer where defects readily generate (such as adjacent to an edge) and for places otherwise, for example, when a large number of the same products are examined.

Into the determining circuit 131, the difference signal of the image signals of the corresponding pixels between of the examination area and of the reference area from the image comparing circuit 121, the threshold value data of the corresponding pixel which is read out from the threshold value storing circuit 123, and the coefficients for changing the threshold value of the corresponding pixel which are entered from the coefficient tables 132, 133 are entered.

The determining circuit 131 generates the threshold value for determination by multiplying the threshold value entered from the image processing device 120 by the coefficients of the corresponding pixel entered from the coefficient tables 132, 133. Then, it compares the difference signal from the image comparing circuit 121 and the threshold value for determination of the corresponding pixel to determine existence of a defect. Here, it determines that the pixel is caused by the scattered light from a defect when the difference signal is equal to or greater than the threshold value for determination and outputs its detection result to the examination result memory device 150. The determining circuit 131 also outputs the information of the threshold value used for determination to the examination result memory device 150.

The coordinate managing device 140 detects the X coordinate and the Y coordinate of the position on which the examination light is currently being irradiated on the wafer 1 based on position information of the wafer stage (that is, position information of the wafer 1), which is entered from the X scale 30 and the Y scale 40, and output the coordinate information to the image processing device 120, the defect decision device 130, and the examination result memory device 150. Also in the coordinate managing device 140 disposition information of the respective examination areas on the wafer 1 is memorized. The disposition information of the respective examination areas memorized in the coordinate managing device 140 is output to the image processing device 120 and the coefficient tables 132, 133, as mentioned above.

The examination result memory device 150 matches and memorizes the examination result entered from the defect decision device 130 and the coordinate information of the corresponding pixel entered from the coordinate managing device 140. The examination result memory device 150 also memorizes the threshold value information entered from the defect decision device 130, which is also related to the examination result or coordinate information of the corresponding pixel.

The examination result also is provided with a function for correcting a shift of a focus of the detection unit caused by variations of atmospheric pressure and temperature in the device.

The examination result display device 160 displays examination result information entered from the examination result memory device 150. It also displays an image of a defect candidate when reviewing the defect candidate. Incidentally, the examination result display device 160 corresponds as an example of a display unit. Further, as written in (4), the illumination unit 300 and the detection unit 400 are configured by combining plural illumination measures and detection measures having the objective lens 20a, the spatial filter 21a, the imaging lens 22a, and the detector 50a exclusively used for the illumination measure 10a and the objective lens 20b, the spatial filter 21b, the imaging lens 22b, and the detector 50b exclusively used for the illumination measure 10b; that is, an individual detection result display and plural detection result synthesized display can be realized when being provided with the plural illumination measures and detection measures.

The input device 170 selects defect candidates from a map in the examination result display device 160 when, for example, a review of examination results is conducted. Or an entry of a defect candidate number is conducted. Further, it inputs a result of decision whether the defect candidate is a defect or a pseudo defect. Incidentally, the input device 170 corresponds as an example of an input unit.

The result processing device 180 deletes a group of the pseudo defects from a group of the defect candidates on the basis of, for example, a result of decision in the input device 170 whether the defect candidate is a defect or a pseudo defect. Further, computation of a threshold value at which a group of pseudo defects is not detected is performed. Incidentally, the result processing device 180 corresponds as an example of a processing unit.

The external computing device 200 performs review of the defect candidates off-line, for example, with the examination result from the examination result memory device 150 and generates examination condition data.

The embodiments of the present invention are not limited to the above-mentioned description and various changes and modifications can be made within the scope of the technological spirit. Further, in this description, attention is directed to a problem that it is unable to use in the scan speed equal to or greater than the line rate of the TDI sensor since the line rate of the TDI sensor and the scan speed become asynchronous to thereby make the image blurred when the examination is implemented, for example, at the scan speed equal to or greater than the line rate of the TDI sensor. Thus, in order to solve such a problem, the objective is set that a high speed examination is made possible without being influenced by the line rate of the TDI sensor. Then, in order to solve the problem of shift in image addition due to the charge accumulation of the TDI sensor while the line rate of the TDI sensor and the stage scan speed are controlled asynchronously, a thin-line illumination is irradiated on the object to be examined to make only an arbitrary pixel line of the TDI sensor receive the scattered light from the object to be examined. Further, there are an aspect and an advantageous effect such that the aspect ratio of a detection pixel size can be controlled by a speed ratio of the line rate of the TDI sensor and the stage scan speed.

There are also an aspect and an advantageous effect such that an examination in which a high examination sensitivity can more readily be obtained (for example, TDI-sensor synchronous scan examination) and an examination in which a high examination speed (high throughput) can more readily be obtained (for example, an examination with TDI-sensor asynchronous scan) can be realized on the same examining apparatus.

Further, the contents disclosed in the description are listed below, for example.

1. An examining apparatus comprising: an illumination unit that irradiates an examination light onto an object to be examined; a detection unit that detects an intensity and a position of a reflected light or a scattered light generated from a surface or near a surface of the object to be examined; a stage unit that loads the object to be examined and varies a moving speed arbitrarily; a control unit that controls the illumination unit, the detection unit, and the stage unit; a processing unit that processes information detected by the detection unit; and a display unit that displays information processed by the processing unit, which is characterized in that the detection unit has a sensor for detecting a light to receive a light on a pixel area of a predetermined portion of the sensor.

2. In the examining apparatus written in the above-mentioned 1, the examining apparatus which is characterized in that the control unit varies an examination speed arbitrarily by changing a ratio of a sensor drive speed of the sensor for detecting the reflected light or the scattered light in the detection unit and an operation speed of the stage unit.

3. In the examining apparatus written in the above-mentioned 1, the examining apparatus which is characterized in that an aspect ratio of a sensor pixel size in the detection unit is changed by changing a ratio of a sensor drive speed in the detection unit and an operation speed of the stage unit in the control unit.

4. In the examining apparatus written in the above-mentioned 1, the examining apparatus which is characterized in that a time delayed integration type image sensor (TDI sensor) is used as a sensor in the detection unit.

5. In the examining apparatus written in the above-mentioned 4, the examining apparatus which is characterized in that an operation speed of the stage unit is set to an arbitrary speed with respect to a drive speed of a TDI sensor in the detection unit.

6. In the examining apparatus written in the above-mentioned 1, the examining apparatus which is characterized in that the illumination unit varies an illumination width with which an examination light is irradiated onto the object to be examined.

7. In the examining apparatus written in the above-mentioned 6, the examining apparatus which is characterized in that the illumination width is set at least to an identical width to a specified pixel width of a sensor in the detection unit or to thinner than the identical width to be irradiated onto an object to be examined.

8. In the examining apparatus written in the above-mentioned 1, the examining apparatus which is characterized in that the display unit displays a group of defect candidates processed in the processing unit and further comprises an input unit for selecting an arbitrary defect candidate from the group of defect candidates displayed on the display unit.

9. In the examining apparatus written in the above-mentioned 1, the examining apparatus which is characterized in that a pixel area of a predetermined portion of the sensor is a predetermined pixel line alone in the sensor.

10. In the examining apparatus written in the above-mentioned 1, the examining apparatus which is characterized in that the sensor is a TDI sensor; and the control unit controls to switch over between a synchronous scan examination mode of the TDI sensor and an asynchronous scan examination mode of the TDI sensor.

11. An examining method of irradiating an examination light onto an object to be examined and detecting an intensity and a position of a reflected light or a scattered light generated from a surface or near a surface of the object to be examined, which is characterized in that a pixel area of a predetermined portion of a sensor for detecting a light receives a light in the detection.

12. In the examining method written in the above-mentioned 11, the examining method which is characterized in that an examination speed can be varied arbitrarily by changing a ratio of a sensor drive speed of the sensor and a moving speed of the object to be examined.

13. In the examining method written in the above-mentioned 11, the examining method which is characterized in that an aspect ratio of a sensor pixel size of the sensor is changed by changing a ratio of a sensor drive speed of the sensor and a moving speed of the object to be examined.

14. In the examining method written in the above-mentioned 11, the examining method which is characterized in that a time delayed integration type image sensor (TDI sensor) is used as the sensor.

15. In the examining method written in the above-mentioned 14, the examining method which is characterized in that a moving speed of the object to be examined is set to an arbitrary speed with respect to a drive speed of the TDI sensor.

16. In the examining method written in the above-mentioned 11, the examining method which is characterized in that an illumination width with which the examination light is irradiated onto an object to be examined can be varied.

17. In the examining method written in the above-mentioned 16, the examining method which is characterized in that the illumination width is set at least to an identical width to a specified pixel width of the sensor or to thinner than the identical width to be irradiated onto an object to be examined.

18. In the examining method written in the above-mentioned 11, the examining method which is characterized in that a group of defect candidates is displayed; and an arbitrary defect candidate from the group of defect candidates which is displayed is selected.

19. In the examining method written in the above-mentioned 11, the examining method which is characterized in that a pixel area of a predetermined portion of the sensor is a predetermined pixel line alone in the sensor.

20. In the examining method written in the above-mentioned 11, the examining method which is characterized in that the sensor is a TDI sensor; and the control unit controls to switch over between a synchronous scan examination mode of the TDI sensor and an asynchronous scan examination mode of the TDI sensor.

INDUSTRIAL APPLICABILITY

The present invention is not limited to examination of semiconductor wafers but can be widely applicable to examination for scratches, defects, contaminations, and the like on the surface of the various objects to be examined such as liquid-crystal substrates, hard disks, photomask substrates, and so on.

REFERENCE SIGNS LIST 1 wafer
2 chip
10a, 10b illumination measure
11a, 11b illumination elevation angle
12a, 12b illumination X-Y direction angle
20a, 20b objective lens
21a, 21b spatial filter
22a, 22b imaging lens
30 X scale
40 Y scale
50a, 50b detector
100 processing device
110 A/D converter
120 image processing device
121 image comparing circuit
122 threshold value computing circuit
123 threshold value storing circuit
130 defect decision device
131 determining circuit
132, 133 coefficient table
140 coordinate managing device
150 examination result memory device
160 examination result display device
170 input device
180 result processing device
200 external computing device
300 illumination unit
400 detection unit
600 wide-width illumination beam
601 TDI transfer direction
602 TDI illumination area
603 TDI output image signal
604 stage moving direction
605, 608 thin-line illumination beam
606 TDI measurement pixel line
607 TDI sensor receiving-light thin-line illumination width

The invention claimed is:

1. An examining apparatus comprising:
an illumination unit that irradiates an examination light onto an object to be examined;
a detection unit that detects light from said object to be examined;
a stage unit that loads said object to be examined and varies a moving speed arbitrarily;
a control unit that controls said illumination unit, said detection unit, and said stage unit; and
a processing unit that processes information detected by said detection unit, wherein:
said detection unit has a sensor for detecting a light to receive a light on a pixel area of a predetermined portion of said sensor, and
said moving speed of said stage unit is faster than a charge transfer speed in a transfer direction of said sensor.

2. The examining apparatus according to claim 1, wherein said control unit varies an examination speed arbitrarily by changing a ratio of said charge transfer speed of said sensor for detecting said reflected light or said scattered light in said detection unit and said moving speed of said stage unit.

3. The examining apparatus according to claim 1, wherein an aspect ratio of a sensor pixel size in said detection unit is changed by changing a ratio of said charge transfer speed in said detection unit and said moving speed of said stage unit in said control unit.

4. The examining apparatus according to claim 1, wherein a time delayed integration type image sensor (TDI sensor) is used as a sensor in said detection unit.

5. The examining apparatus according to claim 4, wherein aid moving speed of said stage unit is set to an arbitrary speed with respect to said charge transfer speed of a TDI sensor in said detection unit.

6. The examining apparatus according to claim 1, wherein said illumination unit varies an illumination width with which an examination light is irradiated onto an object to be examined.

7. The examining apparatus according to claim 6, wherein said illumination width is set at least to an identical width to a specified pixel width of a sensor in said detection unit or to thinner than said identical width to be irradiated onto an object to be examined.

8. The examining apparatus according to claim 1, wherein a pixel area of a predetermined portion of said sensor is a predetermined pixel line alone of said sensor.

9. The examining apparatus according to claim 1, wherein said sensor is a TDI sensor; and
said control unit controls to switch over between a synchronous scan examination mode of said TDI sensor and an asynchronous scan examination mode of said TDI sensor.

10. An examining method which comprises steps of
irradiating an examination light onto an object to be examined; and
detecting light from said object to be examined, wherein:
a pixel area of a predetermined portion of a sensor for detecting a light receives a light in said step of detecting, and
said object to be examined is moved with a moving speed faster than a charge transfer speed in a transfer direction of said sensor.

11. The examination method according to claim 10, wherein
an examination speed can be varied arbitrarily by changing a ratio of said charge transfer speed of said sensor and said moving speed of said object to be examined.

12. The examining method according to claim 10, wherein
an aspect ratio of a sensor pixel size of said sensor is changed by changing a ratio of said charge transfer speed of said sensor and said moving speed of said object to be examined.

13. The examining method according to claim 10, wherein
a time delayed integration type image sensor (TDI sensor) is used as said sensor.

14. The examining method according to claim 13, wherein
said moving speed of said object to be examined is set to an arbitrary speed with respect to a charge transfer speed of said TDI sensor.

15. The examining method according to claim 10, wherein
an illumination width with which said examination light is irradiated onto an object to be examined can be varied.

16. The examining method according to claim 15, wherein
said illumination width is set at least to an identical width to a specified pixel width of said sensor or to thinner than said identical width to be irradiated onto an object to be examined.

17. The examining method according to claim 10, further comprising steps of
displaying a group of defect candidates; and
selecting an arbitrary defect candidate from said group of defect candidates which is displayed.

18. The examining method according to claim 10, wherein a pixel area of a predetermined portion of said sensor is a predetermined pixel line alone of said sensor.

19. The examining method according to claim 10, wherein said sensor is a TDI sensor; and said control unit controls to switch over between a synchronous scan examination mode of said TDI sensor and an asynchronous scan examination mode of said TDI sensor.

20. The examining apparatus according to claim 1, further comprising:

a display unit that displays information processed by said processing unit.

21. The examining apparatus according to claim 20, wherein said display unit displays a group of defect candidates processed in said processing unit, and further comprising an input unit for selecting an arbitrary defect candidate from said group of defect candidates displayed on said display unit.

* * * * *